United States Patent [19]

Cavon

[11] Patent Number: 4,470,160
[45] Date of Patent: Sep. 11, 1984

[54] CAST GEL IMPLANTABLE PROSTHESIS

[76] Inventor: Joseph F. Cavon, 1125 E. 17th St., Suite W124, Santa Ana, Calif. 92701

[21] Appl. No.: 209,021

[22] Filed: Nov. 21, 1980

[51] Int. Cl.³ .......................... A61F 1/00; A61F 1/24; A41C 3/10
[52] U.S. Cl. ............................................. 3/36; 3/1; 128/DIG. 21
[58] Field of Search ................ 3/36, 1; 128/DIG. 21

[56] References Cited

U.S. PATENT DOCUMENTS

| | | | |
|---|---|---|---|
| 3,243,663 | 12/1966 | Cronin | 3/36 |
| 3,600,718 | 8/1971 | Boone | 3/36 |
| 4,019,209 | 4/1977 | Spence | 3/36 |

OTHER PUBLICATIONS

Silastic Block Brand, Bulletin: 51-055A, Dow Corning Publication, Medical Products Business–Dow Corning Corp., Midland, Michigan 48640, May 1963 (2 pages).
Surgitex Implantable Silicone Plastigel, Medical Engineering Corp., 3037 Mt. Pleasant Street, Racine, Wisc., 53404, Feb. 1980 (2 pages).
McGhan Silicone Block Gel Elastomer, McGhan Medical Corp., 700 Ward Drive, Santa Barbara, Ca. 93111, Feb. 1977 (2 pages).
Intrashiel Mammary Inplant, McGhan Medical Corp., 700 Ward Drive, Santa Barbara, CA 93111, Apr. 1980 (2 pages.)
"Silastic Mammary Prosthesis Now Sterile Packaged, Ready to Implant", Medical-Surgical Review, Oct.-Nov. 1971, p. 36.

Primary Examiner—Ronald L. Frinks
Attorney, Agent, or Firm—David O'Reilly

[57] ABSTRACT

A cast elastomer gel implantable prosthesis for implantation in the human body. The cohesive cast gel prosthesis is formed for subcutaneous implantation and may be subsequently coated with a membrane-thin elastomer or a dissolvable envelope so that when it is implanted, it will retain its natural softness after the human tissue capsule forms around the prosthesis.

11 Claims, 4 Drawing Figures

CAST GEL IMPLANTABLE PROSTHESIS

BACKGROUND

This invention relates to gel elastomer implantable prosthesis and, more particularly, relates to subcutaneous gel elastomer implants.

Early on, silicone gel used for cosmetic purposes was in the form of liquids which were injected subcutaneously. However, serious problems developed because of the migration of the silicone gel into surrounding tissue causing granulomas. These problems became so serious that use of liquid gels was all but stopped. To solve the problem of the migration of the liquid gel, several solutions have been proposed and adopted. Among these was the encapsulation of the silicone gel in one or more artificial plastic or silicone envelopes and implanting this prosthesis subcutaneously. This, however, created altogether new problems.

When such implants are used, for example, in mammaplasty procedures, a natural tissue capsule forms around the implant. Since the advent of the envelope-encased implant, doctors have been fighting the problems following these augmentation mammaplasty procedures, particularly because of the firmness caused by the contracture of the natural tissue capsule which is formed and which tightens around the encased implant. The answer to this problem was thought to be an open or closed capsulotomy, leaving the implant intact. The closed capsulotomy procedure consisted of crushing (i.e. breaking up) the natural tissue capsule by manipulation of the tissue or breast. Alternatively, an open or surgical capsulotomy was sometimes performed. However, neither of these procedures have been effective because they do not get rid of the offending foreign body. That is, the body starts the process of forming the natural tissue capsule over again, resulting in contractures producing excessive firmness and deformity and, in some cases, pulling and painful sensations to the patient with distorted and extremely firm results.

One logical way to solve the problem would be to place the implant in the tissue with the envelope and allow it to remain until the natural tissue capsule is formed which usually will occur within approximately six weeks. The silicone envelope could then be removed, allowing the natural tissue capsule to contain the silicone gel without allowing its migration into surrounding tissues. However, of course, this requires a second procedure and there is no guarantee that some migration will still not occur.

Thus, it was determined that the solution to the overall problem was to provide an implant which eliminated the offending foreign body (i.e., the silicone envelope) and provide an implant which would eliminate the possibility of migration.

SUMMARY

The purpose of the present invention is to provide a silicone gel elastomer implantable prosthesis which will maintain the natural softness of the surrounding tissue after implantation.

In order to solve the problem of maintaining the natural softness of the surrounding tissue, a silicone gel elastomer implantable prosthesis, having a cohesive homogeneous construction with or without minimal membrane coating, is the most important feature of the invention proposed herein. The implantable prosthesis disclosed and described herein, is particularly suitable for use in mammaplasty providing softer, natural breasts for women for use in breast augmentation. The principles of the invention involve the use of a cast gel implantable prosthesis which may have a minimal membrane coating, or in the alternative, utilizing an absorbable shell which would be completely dissolved after approximately six weeks or so. Another alternative would be to provide an easily removable artificial envelope of silicone material which could be removed as soon as the natural tissue capsule is formed. In each case, however, the silicone gel implant would be formed of a cohesive gel material, having a predetermined consistency.

Thus, adoption of the cast gel implantable prosthesis of the present invention would result in the removal of the offending foreign body; that is, the artificial envelope which continually causes problems. This would eliminate any further need for manipulating, crushing, squeezing or uncomfortable maneuvers to the breast area to break up the natural tissue capsules. These procedures are destroying the wrong envelope and only provide a temporary solution. By forming the silicone gel implant of a cohesive material having a predetermined consistency, the implant would be contained by the natural tissue capsule and will not migrate into any surrounding tissues, and will, at the same time, maintain the soft, natural feeling of the surrounding tissue.

The manufacturer of the silicone implants and, particularly, those for use in mammaplasty, would comprise mixing a suitable feeling gel having a predetermined consistency and forming it into an implant or prosthesis in a mold. The mold would be designed for various shapes and sizes producing products which would vary in size and shape, depending upon the need. After vulcanizing the prosthesis in the mold, it will be removed and, in some cases, might be treated with a silicone fluid or elastomer to reduce tackiness. The prosthesis is then ready for implantation as is, or may be covered with an easily removable temporary envelope. If an artificial silicone envelope is used, it of course would have to be removed after a predetermined period of time. Possibly, a dissolvable or absorbable type envelope of various types of materials may be used. Alternatively, after the mold process, appropriate coating of the implant could produce or provide an extremely thin, integral layer which would also maintain the natural feeling and not present any type of foreign body producing a double envelope condition, as with previous implants.

Also included in the invention are the incorporation, if desired, of orientation marks in the prosthesis, as well as integrally incorporating fixation patches where needed, in order to position and hold the implant to surrounding tissue. The fixation material, or patches, could be inserted in the gel material prior to vulcanizing of the gel compound. The gel compound is formed and produced to provide a consistency or cross-link density which may be varied to yield different textures of "feeling". The cohesiveness or cross-link density (sometimes called consistency) preferred would be in the range of approximately 0.1 mm–30 mm, as measured with a penetrometer. The important, unique feature is the elimination of any type of permanent envelope forming an offending foreign body from the use in an implant and, particularly, for use in mammaplasty.

The object of the present invention is to provide a cast gel implantable prosthesis which produces the natural feeling of the surrounding tissue.

Another object of the present invention is to provide a cast gel implantable prosthesis without any artificial envelope.

Yet another object of the present invention is to provide a cast gel implantable prosthesis having a predetermined cohesiveness for subcutaneous implantation.

Another object of the present invention is to provide a cast gel implantable prosthesis having integrally incorporated fixation patches.

Yet another object of the present invention is to provide a cast gel implantable prosthesis having a cohesive structure and including a dissolvable or absorbable envelope.

These and other objects of the invention become obvious from the following detailed description of the invention when considered in connection with the accompanying drawings wherein like reference numbers identify like parts throughout.

DESCRIPTION OF THE PREFERRED EMBODIMENTS

Figure 1:
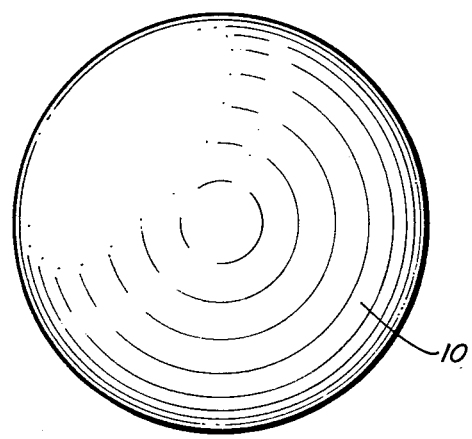
FIG. 1 is a plan view of one prosthesis formed according to the invention.

A cast gel implantable prosthesis which may be coated is illustrated at 10 in FIG. 1 and is comprised of 100% pure silicone gel formed to have a predetermined cohesiveness or cross-link density, sometimes called consistency. The particular implant shown is for augmentation mammaplasty which is the principal use of such prosthesis, but could be formed in any size, or shape for any type of surgical implantation. In the particular implant shown, it is generally circular in shape and has a substantially ovular cross-sectional shape. The prosthesis is manufactured by preparing a compound and mix of a suitable consistency with the cross-link density varied to yield different textures of "feeling". The mixed gel is then poured into a desired mold of which there may be various shapes and sizes to produce products which may be varied according to need. The gel compound is then vulcanized in the mold and removed. The surface of the prosthesis then may be treated with a suitable silicone fluid or elastomer to reduce tackiness. In addition, the implant may have a very thin coating to provide an integral silicone layer or skin, if desired.

Additionally, during the manufacture of the cast gel implantable prosthesis, it may also be provided with a fixation patch as indicted at 18 or at other areas, and a suitable silicone coating or envelope 20. The envelope 20 can be formed of a dissolvable, absorbable material such as gel foam, treated with a topical thrombin to minimize bleeding after insertion, Surgicel (oxidized regenerated cellulose), Dexon (polyglycolic acid), Vicryl (polyglactin), or any other suitable type of absorbable material. The fixation patches could be also comprised of a silicone or Dacron material and are formed integrally with the prosthesis during the molding process. The fixation patch or patches illustrated at or around 18 are for the purpose of holding the implant in position by fibrosis into the fixation patch or patches by localized tissue.

Figure 2:
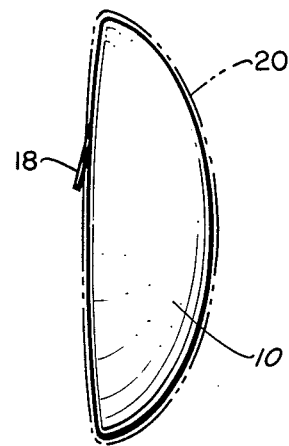
FIG. 2 is a side view of the prosthesis illustrated in FIG. 1.
Figure 3:
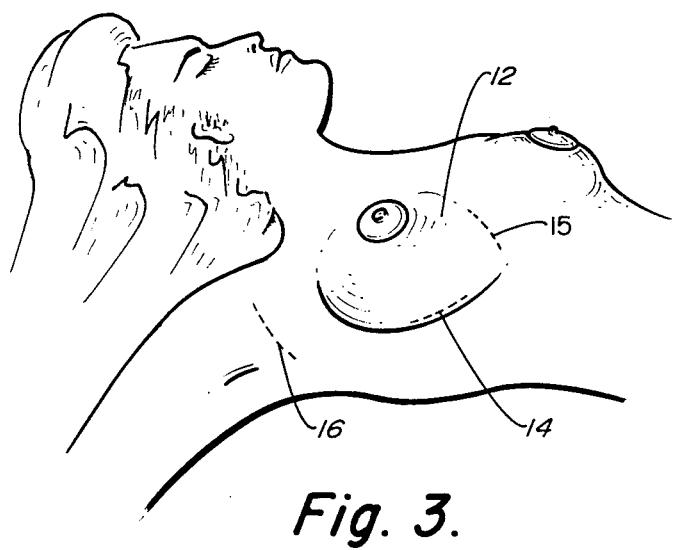
FIG. 3 is a view illustrating the use of the prosthesis shown in FIG. 1 for augmentation mammaplasty operation.
Figure 4:
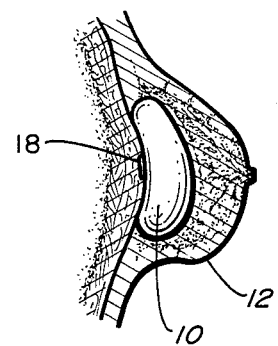
FIG. 4 is a sectional view illustrating the placement of the prosthesis in an augmentation mammaplasty operation.

To illustrate the unique function and method of this invention, FIGS. 3 and 4 show the prosthesis illustrated in FIGS. 1 and 2 used in an augmentation mammaplasty. The augmentation mammaplasty is performed by making incisions near the female breast 12, as shown at the dotted lines at 14, 15 or 16. The augmentation mammaplasty operation will be performed using a 2½ inch inframammary incision, approximately 2 inches lateral to the midline running laterally to approximately 4½" and some 5 centimeters down from the infra-aerola line, following the infra-mammary crease skin line. A pocket is formed beneath the breast, as shown in FIG. 4 and should be made adequately with a sharp and blunt dissection over the fascia of the Pectoralis Major muscle and be large enough to adequately accommodate the desired size of implant in the proper location for proper aesthetic results in the augmentation of the breast 12. After a period of time, a natural tissue capsule will form around this new cohesive cast gel implantable prosthesis and will remain soft insofar as there will not be any artificial envelopes involved in a foreign body reaction. The elimination of the artificial envelope eliminates any need for manipulation or procedures such as open or closed capsulotomies.

The implantation of the cohesive, cast gel implantable prosthesis of the present invention eliminates the problems inherent with the implantation of non-cohesive gels. The non-cohesive gels can migrate into surrounding tissue before a natural tissue capsule is formed to be encapsulated in bizarre places as granulomas. Since the gel was not maintained in the desired position, in a uniform cohesive mass, it was not therefore encapsulated by the natural tissue capsule in one area.

Thus, there has been disclosed a unique way to solve the problem and eliminate the closed or open capsulotomy procedures which destroy or alter the natural tissue capsule, while eliminating the problem of the offending foreign body. This unique way involves implantation procedures as normally done, but also the use of a cohesive, soft, cast gel implantable prosthesis thereby eliminating the body struggle between two or more envelopes fighting each other and producing contracture. A natural tissue capsule will then be formed around the inert, cast gel implantable prosthesis without allowing its migration into surrounding tissue because of its cohesiveness. The implant will therefore remain soft and in proper position giving the result of a natural feeling and natural looking female breast. The method and structure of the prosthesis disclosed herein, of course, may be used for other types of implantation in other body areas.

Therefore, many modifications and variations of the invention are possible in light of the above teachings. It is to be understood that the full scope of the invention is not limited to the details disclosed herein, but only by the claims and may be practiced otherwise than as specifically described.

What is claimed is:

1. A prosthesis for implantation in a human body comprising:
    a homogeneous gel elastomer formed to fit the shape and size of a cavity in the human body;
    said elastomer gel being cohesive and having a consistency as measured by a penetrometer of less than about 30 mm; and a dissolvable envelope around said gel form implant which dissolves in a period of time after implantation.

2. A prosthesis according to claim 1 wherein said gel form implant is substantially circular and has an ovular cross-sectional shape whereby said gel form may be used as a mammary implant.

3. A prosthesis according to claim 2, wherein said gel form implant includes integrally attached fixation patches for securing said implant to body tissue.

4. A prosthesis according to claim 1 wherein said gel form implant has a consistency as measured by a penetrometer in the range of approximately 0.1 mm to 29 mm.

5. The prosthesis according to claim 1 wherein said dissolvable envelope is comprised of a material selected from the group consisting of gel foam, oxidized regenerated cellulose, polyglycolic acid and polyglactin.

6. The prosthesis according to claim 5 including a topical thrombin with said dissolvable envelope to minimize bleeding after implantation.

7. A method of implanting a natural feeling prosthesis in a human body comprising:
   forming said prosthesis of cohesive cast gel in the shape and size desired;
   encapsulating said cohesive cast gel prosthesis in a dissolvable material;
   making an incision in the human body at the area to be implanted;
   inserting said cohesive cast gel implant at the area of the human body desired;
   closing the incision whereby the human body forms a tissue capsule around said cohesive cast gel implant.

8. The method according to claim 7 wherein said step of encapsulating comprises encapsulating said cohesive cast gel implant in a material selected from the group consisting of gel foam oxidized regenerated cellulose, polyglycolic acid and polyglactin.

9. The method according to claim 8 in which said dissolvable material includes a topical thrombin to minimize bleeding after implantation.

10. The method according to claim 7 in which said prosthesis is formed in a substantially circular shape having a substantially ovular cross-sectional shape whereby said prosthesis may be used as a mammary implant.

11. The method according to claim 10 including attaching fixation patches to said prosthesis for securing said prosthesis to body tissue.

* * * * *